US009024107B1

(12) United States Patent
Pero

(10) Patent No.: US 9,024,107 B1
(45) Date of Patent: May 5, 2015

(54) ABSORBENT AND IMPERMEABLE SEAT INSERT

(71) Applicant: Tonya D. Pero, White, GA (US)

(72) Inventor: Tonya D. Pero, White, GA (US)

(*) Notice: Subject to any disclaimer, the term of this patent is extended or adjusted under 35 U.S.C. 154(b) by 258 days.

(21) Appl. No.: 13/856,625

(22) Filed: Apr. 4, 2013

(51) Int. Cl.
*A61F 13/15* (2006.01)
*A61F 13/53* (2006.01)
*A61F 13/47* (2006.01)
*A61F 13/45* (2006.01)

(52) U.S. Cl.
CPC .............. *A61F 13/53* (2013.01); *A61F 13/4704* (2013.01); *A61F 2013/530481* (2013.01); *A61F 2013/530788* (2013.01); *A61F 2013/4518* (2013.01); *A61F 2013/4512* (2013.01); *A61F 13/47* (2013.01)

(58) Field of Classification Search
CPC ................ A61F 2013/4512; A61F 2013/4518; A61F 13/47; A61F 13/4704; A61F 2013/530481; A61F 2013/530788
USPC .............................. 604/358, 385.01, 367, 368
See application file for complete search history.

(56) References Cited

U.S. PATENT DOCUMENTS

| 3,916,447 | A | | 11/1975 | Thompson | |
|---|---|---|---|---|---|
| 4,441,451 | A | * | 4/1984 | Neal | 119/168 |
| 4,759,086 | A | * | 7/1988 | Booth-Cox | 4/451 |
| 4,943,105 | A | * | 7/1990 | Kacar et al. | 296/24.31 |
| 5,482,007 | A | * | 1/1996 | Kumlin | 119/169 |
| 6,523,187 | B1 | * | 2/2003 | Brink et al. | 4/484 |
| 7,367,621 | B1 | * | 5/2008 | Han-Dressor et al. | 297/256.17 |
| 7,655,829 | B2 | | 2/2010 | MacDonald et al. | |
| 7,726,260 | B1 | | 6/2010 | Yananton | |
| 2007/0152410 | A1 | * | 7/2007 | Clark et al. | 280/33.992 |
| 2009/0165199 | A1 | * | 7/2009 | Heumann | 4/483 |

* cited by examiner

*Primary Examiner* — Jacqueline Stephens
(74) *Attorney, Agent, or Firm* — Crossley Patent Law

(57) ABSTRACT

An absorbent and impermeable seat insert that includes a front edge, a rear edge, and a pair of side edges, each of a pair of side walls erectable along each of the pair of side edges and a rear wall erectable along the rear edge, said seat insert having an impermeable bottom layer disposed underlying an absorbent cardboard layer, and a gelling layer disposed to absorb and retain fluids introduced into the seat insert, wherein a dry weave disposed atop the gelling layer wicks fluids introduced onto the seat insert into the gelling and cardboard layers, where said fluid is retained and prevented from transmission through to an underlying seat by means of the impermeable layer, whereby a particular seat is protected from the inadvertent release of bodily fluids by an incontinent individual or by a child during potty training.

6 Claims, 4 Drawing Sheets

ABSORBENT AND IMPERMEABLE SEAT INSERT

BACKGROUND OF THE INVENTION

Various types of seat covers are known in the prior art. However, what is needed is an absorbent and impermeable seat insert configurable for use upon a particular seat to protect said seat from bodily fluids inadvertantly released thereupon by a small child or incontinent individual.

FIELD OF THE INVENTION

The present invention relates to an absorbent and impermeable seat insert, and more particularly, to an absorbent and impermeable seat insert that includes a front edge, a rear edge, and a pair of side edges, each of a pair of side walls erectable along each of the pair of side edges and a rear wall erectable along the rear edge, said seat insert having an impermeable bottom layer disposed underlying an absorbent cardboard layer, and a gelling layer disposed to absorb and retain fluids introduced into the seat insert, wherein a dry weave disposed atop the gelling layer wicks fluids introduced onto the seat insert into the gelling and cardboard layers, whereat said fluid is retained and prevented from transmission onto an underlying seat by means of the impermeable layer, whereby a particular seat is protected from the inadvertent release of bodily fluids by an incontinent individual or child during potty training.

SUMMARY OF THE INVENTION

The general purpose of the absorbent and impermeable seat insert, described subsequently in greater detail, is to provide an absorbent and impermeable seat insert which has many novel features that result in an absorbent and impermeable seat insert which is not anticipated, rendered obvious, suggested, or even implied by prior art, either alone or in combination thereof.

The present absorbent and impermeable seat insert has been devised for use with young children or incontinent individuals to protect an underlying seat from contamination with bodily fluids should such a person seated thereupon lose control of their bodily functions.

The present absorbent and impermeable seat insert is adapted for positioning upon a particular seat, and includes a front edge, a rear edge, and a pair of slide edges. The rear edge and each of the pair of side edges are foldable into an upright position to form each of a rear wall and a pair of side walls that bound the seat insert on three sides. The absorbent and impermeable seat insert is contemplated for use upon all extant seats, and may be produced in different sizes for incontinent adults. However, the preferred embodiment herein disclosed illustrates an absorbent and impermeable seat insert configured to use with a small child during potty training who, although out of diapers, may nonetheless have an accident while seated in a particular chair or seat, such as a child seat, a sofa or chair, or even a child safety seat for use in vehicles.

An impermeable bottom layer is disposed upon the seat insert to prevent fluids from passing through the seat insert onto said underlying seat. An absorbent cardboard layer is disposed atop the impermeable layer to absorb and retain fluids within the seat insert. And a gelling material is disposed atop the cardboard layer, said gelling material absorbing fluids introduced onto the seat insert and retaining them therein. A dry weave is disposed atop the gelling material to wick fluids into the seat insert. By presenting a compressible substrate atop a particular chair, the gelling material and cardboard layer also provide for an amount of comfort for a person seated upon the seat insert.

To secure the absorbent and impermeable seat insert in position atop a particular seat, a pair of adhesive strips is disposed on the bottom layer to contact the seat upon which the device is positioned. A pair of backing members is disposed to cover the pair of adhesive strips and preserve the adhesive there disposed until the device is readied for use. Each of the pair of backing strips is thus removable to reveal the adhesive strips when the device is readied for use, whereby the seat insert is releasably securable atop a seat surface, as desired.

An embodiment is contemplated for use with child safety seats in vehicles. This embodiment includes a pair of perforations disposed in the seat insert in parallel, perpendicularly rendered from the front edge. Each of the pair of perforations enables selective tearing of the seat insert along each of said pair of perforations, and a crotch portion is thereby erectable between each of said pair of perforations when torn, whereby an extant seat belt may be buckled between the legs of a child seated upon the seat insert, said seat insert positioned upon a child safety seat in a vehicle.

Thus has been broadly outlined the more important features of the present absorbent and impermeable seat insert so that the detailed description thereof that follows may be better understood and in order that the present contribution to the art may be better appreciated.

Objects of the present absorbent and impermeable seat insert, along with various novel features that characterize the invention are particularly pointed out in the claims forming a part of this disclosure. For better understanding of the absorbent and impermeable seat insert, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
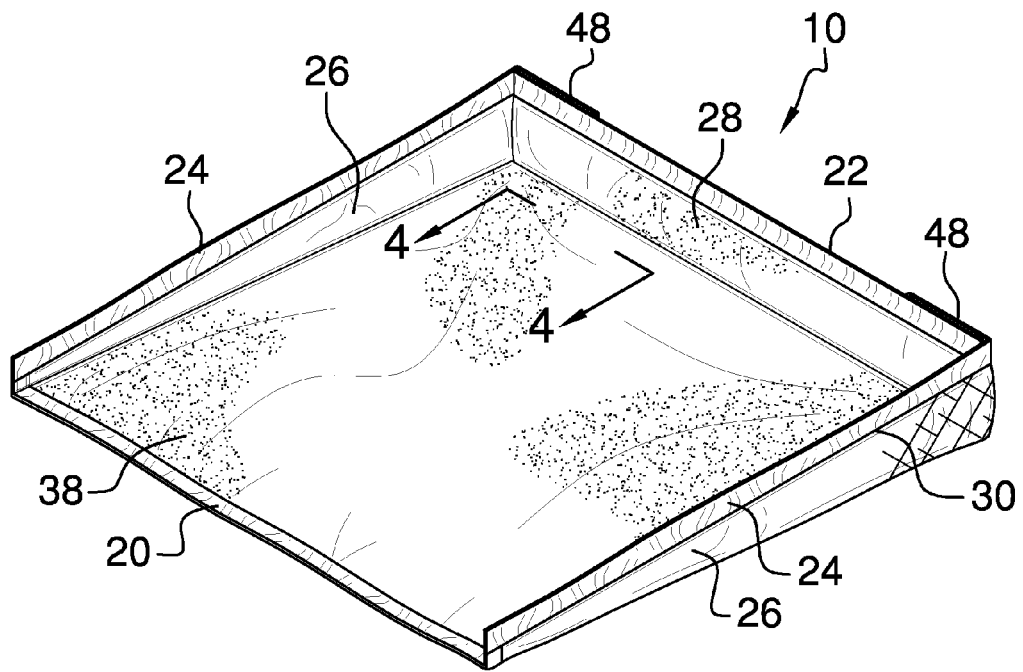
FIG. 1 is an isometric view.
Figure 2:
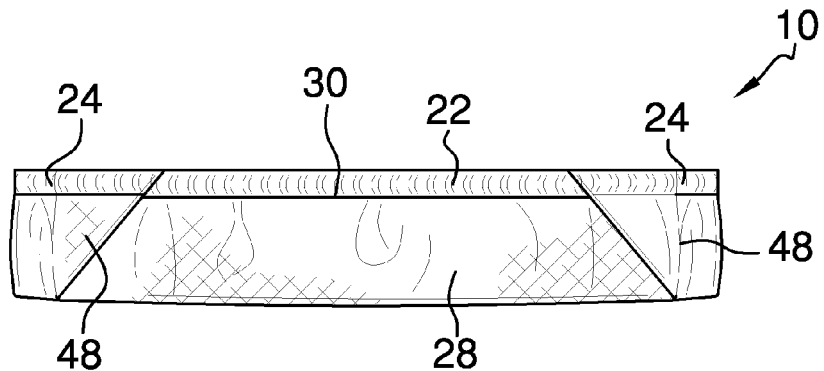
FIG. 2 is a rear view.

With reference now to the drawings, and in particular FIGS. 1 through 6 thereof, example of the instant absorbent and impermeable seat insert employing the principles and concepts of the present absorbent and impermeable seat insert and generally designated by the reference number 10 will be described.

Referring to FIGS. 1 through 6 a preferred embodiment of the present absorbent and impermeable seat insert 10 is illustrated.

The present absorbent and impermeable seat insert 10 has been devised as a tool for parents to use when potty training young children. However, embodiments of the device 10 are considered for use with incontinent adults, the scale and size of the present device readily adaptable to accommodate an older person, as desired during manufacture.

The present invention 10 is an erectable, absorbent, and impermeable seat insert 10 configurable for use upon a particular seat, as desired, to protect said underlying seat from any fluids inadvertently produced by a child (or incontinent individual) seated thereupon when not wearing a diaper. The absorbent impermeable seat cover 10 has been devised to absorb any such fluids and prevent the passage of said fluids through to the underlying surface, whereby parents (or caregivers) may protect an underlying seat during their child's transition away from wearing diapers.

The present absorbent and impermeable seat insert 10, then, includes a front edge 20, a rear edge 22, and a pair of side edges 24. The absorbent and impermeable seat insert 10 is foldable along lines parallel to each of the pair of side edges 24 to erect each of a pair of side walls 26 along each of the pair of side edges 24. A rear wall 28 is likewise foldable along the rear edge 22. Each of said pair of side walls 26 and rear wall 28 therefore bound three sides of the seat insert 10 when in use. A longitudinal stiffener 30 is disposed along each of the pair of side edges 24 and rear edge 22 to strengthen each of the respective side walls 26 and rear wall 28 when erected to prevent sagging.

To fold the seat insert 10 for use, the rear wall 28 is erected and then each of the pair of side walls 26 is likewise erected. Each of a pair of tab members 48, disposed endwise on each of the pair of side walls 26 is then folded to engage against the rear wall 28 and maintain closure between each of the pair of side walls 26 and the rear wall 28 (see FIG. 2). In the preferred embodiment shown in FIG. 1, each of the pair of side walls 26 has a shorter height proximal the front edge 20 relative a longer height proximal the rear edge 22. It should be noted that an embodiment is contemplated that, in use, raises the front edge 20 into a plane disposed above the portion of the seat insert 10 disposed directly underneath the rear wall 28 when erected, whereby fluids introduced into the seat insert 10 are drawn under the influence of gravity away from the front edge 20.

An impermeable bottom layer 32 is provided to prevent leakage of fluids retained by the device 10. A bleached cardboard layer 34 is disposed atop the impermeable bottom layer 32 and a gelling material 36 is disposed atop the cardboard layer 34. Each of the cardboard layer 34 and gelling material 36 absorb fluids and retain said fluids within the device 10 atop the impermeable bottom layer 32. A dry weave 38 is disposed atop the gelling material 36 to wick fluid interiorly into the gelling material 36 and move fluids away from a child seated atop the device 10.

Figure 3:
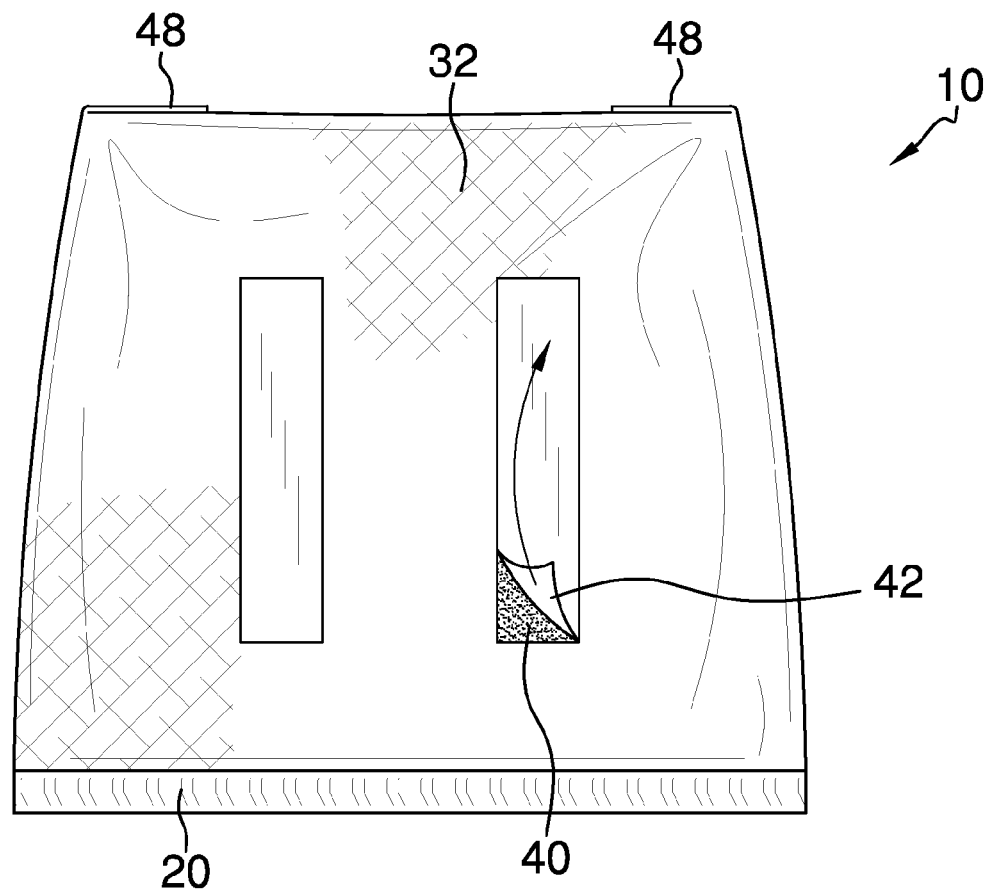
FIG. 3 is a bottom view.
Figure 4:
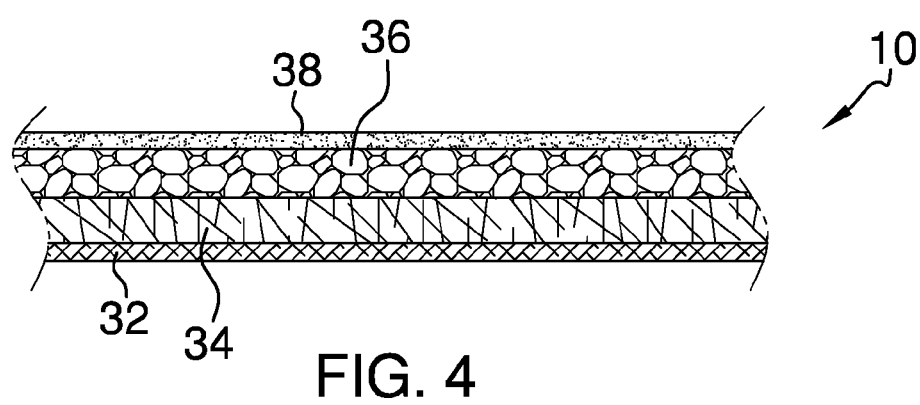
FIG. 4 is a cross-section view taken along the line 4-4 of FIG. 1.
Figure 5:
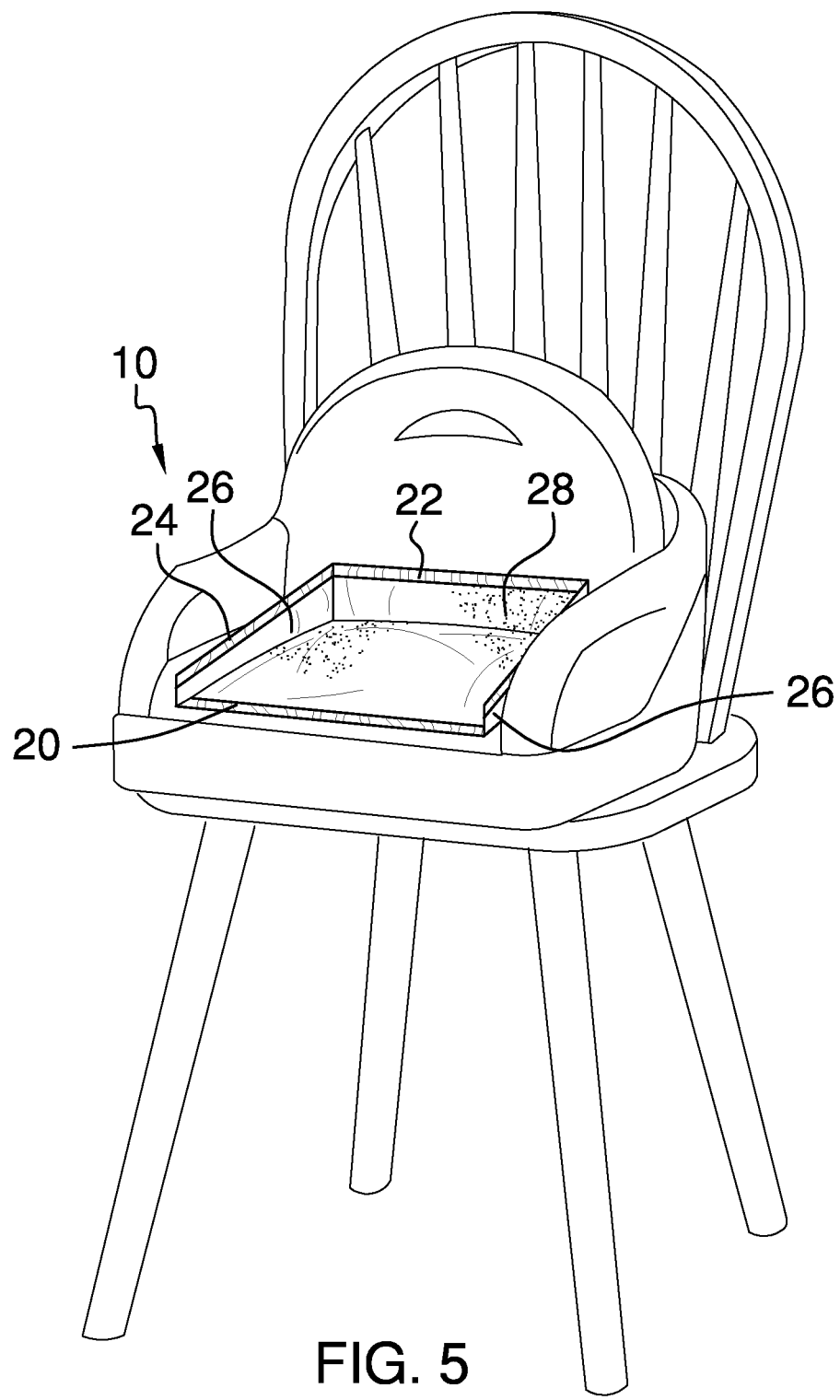
FIG. 5 is an in-use view.

To releasably secure the device 10 in position atop a particular seat during use, a pair of adhesive strips 40 is disposed on the impermeable layer (see FIG. 3). Each of said pair of adhesive strips 40 is disposed to contact an extant seat atop which the seat insert 10 is situated. Each of a pair of backing members 42 is disposed covering each of the pair of adhesive strips 40, said backing members 42 revealing an adhesive layer when removed therefrom, whereby the seat insert 10 is securably positional atop an extant seat.

Figure 6:
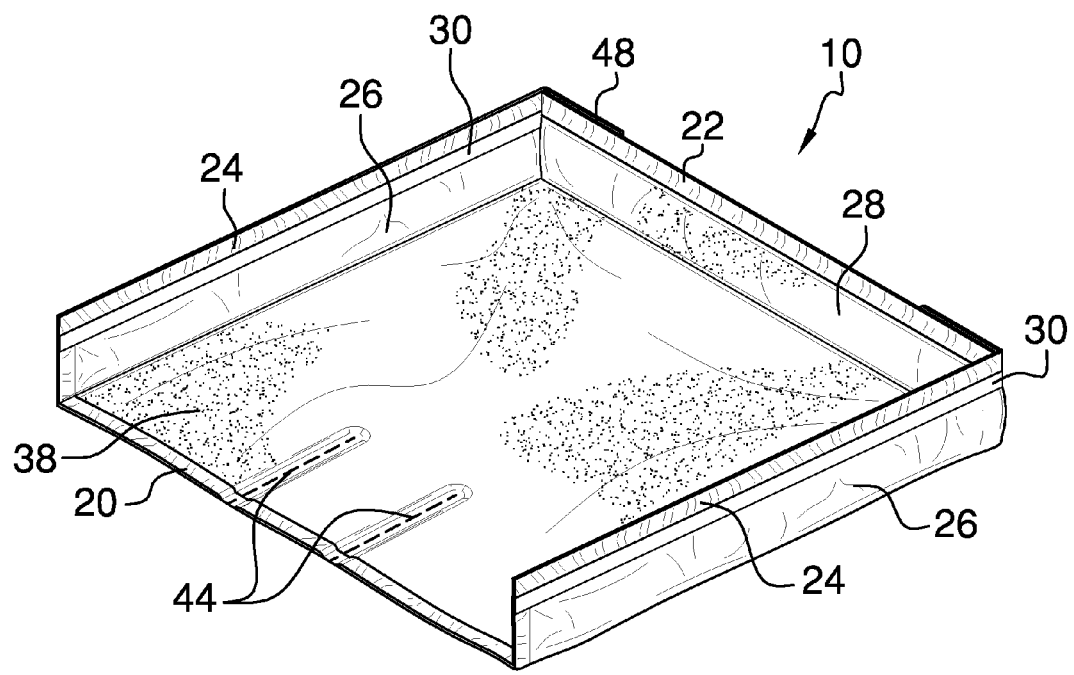
FIG. 6 is an isometric view of an alternate embodiment.

Referring to FIG. 6, an alternate embodiment is illustrated for use with an extant car seat (not shown). A pair of perforations 44 is contemplated disposed in parallel, each of said pair of perforations 44 perpendicularly rendered in the seat insert 10 from front edge 20. Each of said pair of perforations 44 is capable of tearing and a crotch portion 46 is thereby positional raised up between a toddler's legs, when said toddler is seated upon the seat insert 10, to accommodate the interconnection of an extant seat belt fastener (not shown) disposed upon an extant car seat (not shown) upon which the seat insert 10 may be situated.

What is claimed is:

1. An erectable absorbent and impermeable seat insert configurable for use upon a particular seat, said absorbent and impermeable seat insert comprising:
    an impermeable bottom layer;
    a bleached cardboard layer disposed atop the impermeable layer;
    a gelling material disposed atop the cardboard layer; and
    a dry weave disposed atop the gelling material;
    wherein the absorbent and impermeable seat insert is foldable to erect a pair of side walls having a rear wall disposed therebetween, each of said pair of side walls and rear wall bounding three sides of the seat insert, whereby said cardboard layer and gelling material absorb fluids excreted atop said seat insert and the impermeable bottom layer prevents fluids from leaking through the gelling material and onto an underlying seat upon which the absorbent impermeable seat insert is disposed.

2. The absorbent and impermeable seat insert of claim 1 further comprising a pair of adhesive strips disposed upon an underside of the seat insert, said strips configured to releasably secure the seat insert in position upon an extant seat when each of a pair of backing members is removed from covering each of the pair of adhesive strips and an adhesive layer is thereby exposed.

3. The absorbent and impermeable seat insert of claim 2 further comprising a pair of perforations disposed in the seat insert, each of said perforations disposed perpendicularly from a front edge of the seat insert, whereby a crotch portion is uplifted, as desired, to accommodate interconnection of an extant seat belt fastener disposed upon an extant car seat to which the seat insert is fitted.

4. The absorbent and impermeable seat insert of claim 3 further comprising a longitudinal stiffener disposed along each of the pair of side walls and the rear wall whereby each of said walls is stabilized bordering the seat insert on three sides.

5. An erectable absorbent and impermeable seat insert configurable for use upon a particular seat, said absorbent and impermeable seat insert comprising:
    a front edge, a rear edge, and a pair of side edges;
    an impermeable bottom layer;
    a bleached cardboard layer disposed atop the impermeable layer;
    a gelling material disposed atop the cardboard layer;
    a dry weave disposed atop the gelling material;
    a pair of adhesive strips disposed on the impermeable layer, each of said pair of adhesive strips disposed to contact an extant seat atop which the seat insert is situated;
    each of a pair of backing members disposed covering each of the pair of adhesive strips, said backing members revealing an adhesive layer when removed therefrom, whereby the seat insert is securably positional atop an extant seat; and
    a longitudinal stiffener disposed along each of the pair of side edges and rear edge;
    wherein the absorbent and impermeable seat insert is foldable to erect a pair of side walls along each of the pair of side edges and a rear wall along the rear edge, each of said pair of side walls and rear wall bounding three sides of the seat insert, whereby said gelling material absorbs fluids excreted atop said seat insert and the impermeable bottom layer prevents fluids from leaking through the gelling material and onto an underlying seat upon which the absorbent impermeable seat insert is disposed.

6. The absorbent and impermeable seat insert of claim 5 further comprising a pair of perforations disposed in parallel, perpendicularly rendered in the seat insert from the front edge, each of said pair of perforations capable of selective tearing to raise a crotch portion between a toddler's legs, when said toddler is seated upon the seat insert, to accommodate the interconnection of an extant seat belt fastener disposed upon an extant child safety seat for vehicles.

* * * * *